United States Patent [19]

Burtscher et al.

[11] Patent Number: 4,837,440
[45] Date of Patent: Jun. 6, 1989

[54] METHOD AND APPARATUS FOR CHARACTERIZATION OF AEROSOLS

[75] Inventors: Heinz Burtscher; Adnreas Schmidt-Otl; Hans-Christoph Siegmann, all of Zurich, Switzerland

[73] Assignee: Matter & Siegmann AG, Wohlen, Switzerland

[21] Appl. No.: 926,903

[22] Filed: Nov. 3, 1986

Related U.S. Application Data

[63] Continuation-in-part of Ser. No. 732,858, May 10, 1985, abandoned.

[30] Foreign Application Priority Data

May 11, 1984 [DE] Fed. Rep. of Germany ....... 3417525

[51] Int. Cl.⁴ ............................................. G01N 27/64
[52] U.S. Cl. .................................. 250/379; 250/382; 250/423 P; 324/464
[58] Field of Search ................... 250/423 P, 372, 379, 250/387, 382; 324/464, 465, 466

[56] References Cited

U.S. PATENT DOCUMENTS

| | | | |
|---|---|---|---|
| 3,933,432 | 1/1976 | Driscoll | 250/423 P |
| 4,232,225 | 11/1980 | Randhawa | 250/361 C |
| 4,463,595 | 8/1984 | Yeh et al. | 73/863,33 |
| 4,570,494 | 2/1986 | Dunn et al. | 73/863.21 |
| 4,574,004 | 3/1986 | Schmidt-Ott et al. | 250/503.1 |
| 4,769,548 | 9/1988 | Burtscher et al. | 250/423 P |

OTHER PUBLICATIONS

Burtscher et al., "Probing Aerosols by Photoelectric Charging", J. Appl. Phys. 53 (5), May 1982, pp. 3787–3791.

Weeks et al., "Interaction of TEA $CO_2$ Laser Radiation with Aerosol Particles", Appl. Optics, 15 (1), Nov. 1976, pp. 2917–2921.

*Primary Examiner*—Carolyn E. Fields
*Attorney, Agent, or Firm*—Tarolli, Sundheim & Covell

[57] ABSTRACT

Aerosol particles, resulting from the combustion of organic substances with insufficient oxygen supply, usually contain toxic, higher hydrocarbonic substances (e.g. tar) on their surface. These substances, e.g. tar, has the property to be photoelectrically more active than other substances contained in the atmosphere. In the method and apparatus according to the invention an aerosol, i.e. the carrier gas containing the particles to be characterized, is used which has been brought to at least one predetermined temperature sufficient for evaporation or decomposition or preventing condensation of molecules on particles of said aerosol that quench or enhance photoelectric activity. Such aerosol is exposed to electromagnetic radiation and, thereby, activated to electron emission. Thereafter the charge of the photoelectrically positively charged particles is determined by means of size selective filter means which are connected to current or charge measuring equipment. From the measured values information can be derived about the nature and amount of said molecules and about the remaining surface of the aerosol particles. Additional information on the coatings and also on the species of hydrocarbon may be obtained by observing the measured values as a function of temperature. The method and apparatus are particularly useful for the measurement of air pollution.

15 Claims, 3 Drawing Sheets

METHOD AND APPARATUS FOR CHARACTERIZATION OF AEROSOLS

This is a continuation-in-part of copending application Ser. No. 732,858 filed on May 10, 1985 now abandoned.

BACKGROUND OF THE INVENTION

1. Field of the Invention

During the combustion of wood, coal, natural gas, mineral oil and other substances as well as during the smoking of cigarettes, non-combustible residues in the form of more or less fine suspended particles escape into atomphere. If the combustion process is not supplied with enough oxygen or if the combustion process is performed with a controlled deficiency of oxygen, as e.g. during the diffusion flame of a wood fire or during the glowing combustion of a cigarette, additionally coal (soot), carbonmonoxide and hydrocarbons are produced. In the hot part of the combustion, the core of the particles consisting of coal or ash is formed. As soon as the exhaust gases of the combustion cool down, the hydrocarbons, if present due to lack of oxygen, condense on the surface of these cores. Other, more volatile substances such as water or acids may condense together or on top of these. The chemical and toxical properties of the suspended particles, their ability to act as condensation nuclei and their role in the production of photochemical smog mainly depend on the nature of their surface, the thickness of the surface layer involved and on the nature of the process. In contrast, the diffusion of particles as well as their probability of deposition in a filter depends only on their size and not on their surface composition.

2. Prior Art

The quantitative characterization, i.e. the characterization of the size of aerosols, i.e. of particles which are suspended in a carrier gas, is well known in the prior art and does not offer any fundamental technical problems. Usually such measurements are performed by measuring the diffusion constant or the electrical mobility of charged particles. In contrast the chemical classification, i.e. the qualitative characterization of suspended particles, is very difficult to perform. Chemical characterization is possible with condensed particles only, whereby particularly the most important information about the nature of the substances present on the surface of the particles is lost. The mixture of unvolatile, high molecular mass hydrocarbons, e.g. polyaromatic hydrocarbons (henceforth in short called PAH), which is produced during combustion and which condenses on the surface of the particles, contains carcinogenic and other toxic compositions, which are only present in very small amounts, but which can create a very high activity, being exposed at the surface of the particles.

A surface sensitive method for the characterization of such particles as well as an apparatus for carrying out such method, therefore, is urgently needed, since such particles, mainly contained in exhaust gases of industry and of automobilies, represent the most important part of air pollution. Among hydrocarbons resulting from a combustion process there are always such substances which have, as surface layers or adsorbates, the tendency to easily supply electrons. This property results in enhanced chemical activity and in a low work function. In other words, they show a pronounced photoelectric effect.

The photoelectric effect of particles suspended in the atmosphere has been systematically examined, for the first time, 1981 and has been described in the publication "H.Burtscher er al., J.Appl.Phys.53, 3787(1982)". The apparatus used there contains an ozone-free low pressure ultraviolet lamp. The air with the suspended particles flows past this lamp. Thereby, photoelectrically active particles emit electrons and the particles become positively charged. The charge on those particles create an electric current in a subsequent filter, which current is proportional to the photoelectric activity of the aerosol. In order to present condensation of water on the surface of insulation elements within the system, the incoming aerosol is heated to a temperature slightly above ambient.The presumption expressed in the aforementioned publication, namely that the particles of the atmosphere having a high photoelectric activity contain PAH, has been confirmed in subsequent examinations.

Further investigations have shown that other components found in the atmosphere like water, acids or aliphatic hydrocarbons may adsorb with, or on top of the PAH's and quench photoelectric activity. The apparatus described in the above publication, therefore, is not applicable to quantitative measurements because of the interference between those components activating photoemission with those quenching it.

OBJECTS OF THE INVENTION

On the basis of the aforementioned prior art, it is an object of the present invention to provide method and apparatus for the mainly quantitative rather than merely qualitative characterization of aerosol particles, particularly of PAH-containing particles, using the principles of photoelectric charging of aerosol particles known per se. Thereby the degree of the pollution of the environment by such chemically active particles may be measured. It is a further object of the invention to improve method and apparatus of the aforementioned kind, using further and recently found knowledge, and to make possible the acquisition of more precise information on the particle surface. Particularly it is a further object in connection with said method or apparatus to enhance to sentivity thereof such that hydrocarbon loaded particles are detectable even in what is usually called "pure" air.

It is a still further object of the invention to provide method or apparatus of the aforementioned kind being particularly capable of detecting and characterizing particles which easily are aspirated into the lungs.

Furthermore it is an object of the invention to make possible also the acquisition of information about said deactivating components As to the apparatus, it is an object of the invention to allow for particle size discrimination in connection with the surface characterization thereof.

A still further object of the invention is to provide an apparatus of the aforementioned kind which can be operated during all weather conditions and which has a compact size.

SUMMARY OF THE INVENTION

In performing the aforementioned objects and other ones, the invention provides method and apparatus for the quantitative and qualitative characterization of hydrocarbon containing particles suspended in a carrier gas, e.g. in the ambient air.

An essential feature in performing the objects consists in using an aerosol, which had been brought to at least one predetermined temperature sufficient for evaporation or decomposition or preventing condensation of molecules on particles of said aerosol. There may be present such molecules which are quenching and such which are enhancing the photoelectric activity and, accordingly, the electron emission induced by irradiation. In both cases the measured charge values of the aerosol particles offer information not only on the number of particles, but also on the nature of the remaining particle surface. Furthermore, because the evaporation or decomposition temperatures of a great variety of substances are well-known, by means of multiple measurements using the same aerosol under different temperature conditions, ample information about the nature and amount of said molecules is available with the air of the present invention..

Particularly aromatic and, more specifically, polyaromatic hydrocabons and their derivates have been found to exert enhancing effects on the photoelectric activity and/or the photoemission of electrons on the particle surface. On the other hand, a greater variety of substances has revealed to be quenching the photoelectric activity and photoemission. This group of substances comprises particularly aliphatic and other non-aromatic hydrocarbons and derivates thereof as well as inorganic acids and water.

Accordingly, the method and apparatus according to the invention are particularly capable of detecting aerosols with aprticles carrying hydrocarbon compounds. In this context the detection of polyaromatic hydrocarbons (in short: PAH) is of special interest.

The apparatus a gas flow system comprising aerosol heating means for thermal particle-modification and an activation chamber is provided with electromagnetic radiation means for activating to electron emission and electrically charging the aerosol particles to be detected and characterized. Typically an ultraviolet radiation source is provided for photoelectrically activating said particles. The apparatus further comprises means for particle collection and charge detection. Typically said thermal particle-modification means is installed such that the temperature of the aerosol in and/or before the irradiated zone can be varied so as to evaporate adsorbates or condensates on the particle surface.

In a preferred embodiment of the invention representing the best mode of operation, the apparatus comprises an essentially closed chamber, having a gas inlet and a gas outlet as well as an activation chamber which is sonfined by two gas pervious light sluices. An ultraviolet radiation source is mounted in operative connection with the irradiation zone, wherein the aerosol is exposed to the ultraviolet radiation.

The irradiation zone comprises at least partially a wall surface which is held on a defined electric potential and which has a conductivity that is high enough to conduct the charge of the small ions produced by photoemission and moving to said wall surface to said defined electric potential. Moreover, the wavelength of the radiation should be selected such that the photon energy is smaller than the ionization potential of the gas molecules in order to avoid or reduce disturbances in the selective aerosol particle activation and characterization due to the formation of small ions.

In the preferred embodiment said particle collection and charge detection means comprise at least one collector electrode arranged in the region of the gas outlet of the activation chamber, said collector electrode being electrically connected to a current or charge meter. Preferably the collector electrode is mounted to the wall of the outer chamber by means of water repelling insulating members.

Further there are provided means perferably arranged in the region of the inlet of the system or of the activation chamber for electrically neutralizing the particle contained in carrier gas entering the activation chamber.

The apparatus according to the invention has excellent sensitivity properties as to particle size so to concentration. Experience has shown that it was possible to detect the existence of particles with a concentration of 10 particles per $cm^3$ with a diameter of between 5 and 10 nanometers. The sensitivity of the apparatus is lower for particles having a diameter of more than 10 micrometers since the photoelectron has a high probability to diffuse back to the particle.

Further preferred embodiments of the apparatus are furnished with size-selective filter means for aerosol particle size discrimination. In principle, such selection may be performed by restricting the collection and charge detection to particles of a predetermined size range as well as by pre-collection and exclusion of predetermined size ranges from the following charge detection. When adopting the first-mentioned variation, the collector electrode can be designed so as to include or consist of a size-selective filter element.

At least one electrostatic shielding means shields said collector electrode from the fan and/or from the ultraviolet radiation source.

In order to produce a gas flow through the chamber, there is provided a fan and preferably control means connected to said fan for producing a controllable flow of carrier gas through the system.

Beside the application of the aforementioned apparatus as a means for the detection of pollution of the ambient air or the pollution of the air at a working place by industrial processes, it is also possible to use the apparatus in the laboratory to characterize artificially produced aerosols.

The apparatus can easily be operated and does not need a great effort in maintenance.

BRIEF DESCRIPTION OF THE DRAWINGS

The enclosed drawings show different embodiments of the invention, which will be described in the following specification. In the drawings.

DESCRIPTION OF THE PREFERRED EMBODIMENTS

Figure 1:
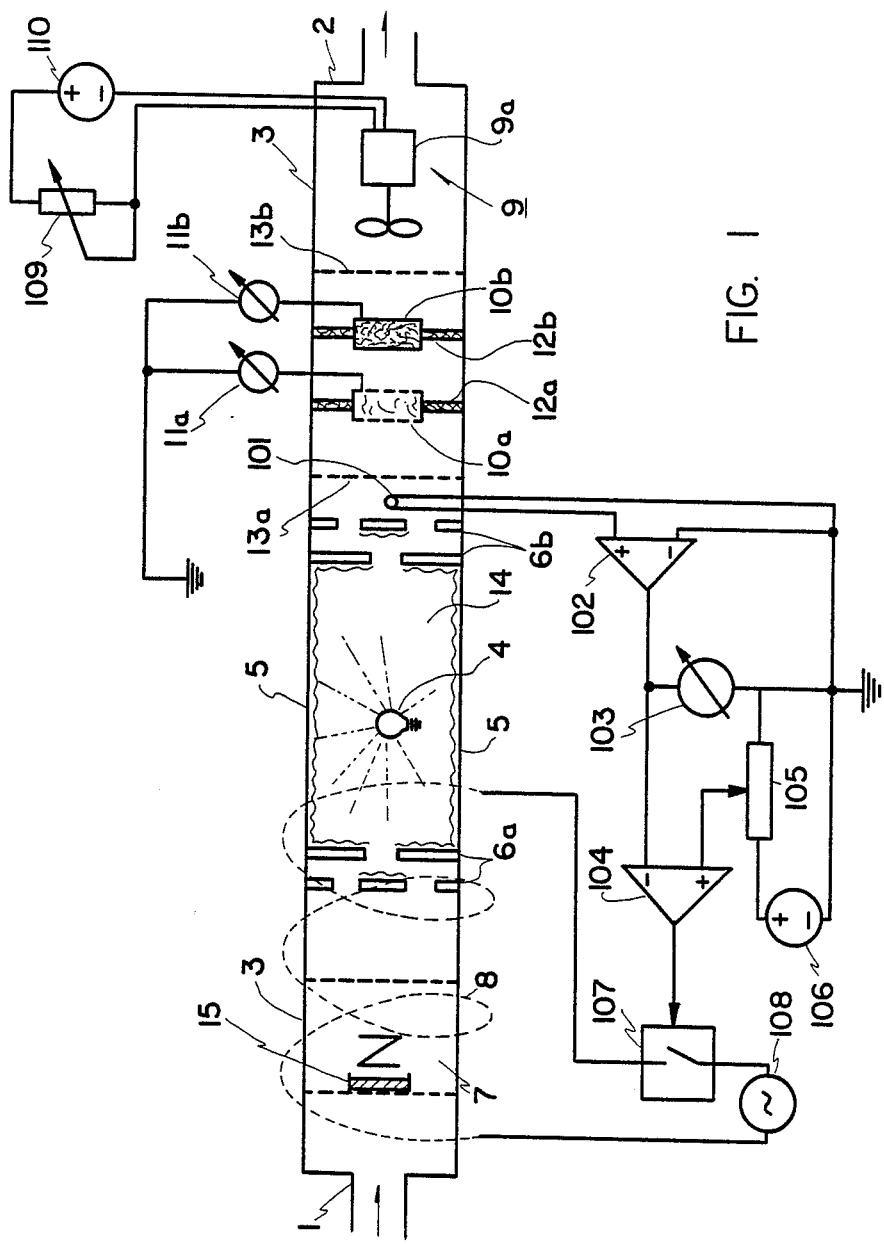
FIG. 1 a shows a schematic sectional view along the longitudinal axis of the processing chamber together with a functional block diagram of the apparatus for a first embodiment.

As can be seen in FIG. 1, the first embodiment of the apparatus according to the invention comprises an essentially cylindrical chamber 3 having an inlet portion 1 and an outlet portion 2. The carrier gas incorporating the aerosol to be characterized is fed to the inlet portion 1 by suitable feeding means not further shown in the drawing, passes the interior of the chamber 3 by flowing from the inlet portion 1 thereof to the outlet portion 2 and leaves the chamber 3 through a duct arranged in the region of the outlet portion 2. The interior of the chamber 3 receives an ultraviolet radiation source, e.g. in form of a lamp 4. The radiation emitted by the lamp 4 is in a wave lenght range and emits photoenergies equivalent to photon energies, which are below the ionisation energy of the carrier gas and above the work function of particles to be characterized.

Furthermore the ultraviolet radiation source is characterized by the fact that it does not initiate any photochemical reactions which chemically change the surface of the particles. Such reactions would falsify the results of the measurements. If air is used as a carrier gas, commercially available ozone-free low pressure bulbs may be used as they meet these requirements. Another possibility to avoid or quench such photochemical reactions is to use a flash bulb, e.g. a xenon high pressure bulb. Such bulbs create a very intense radiation during a very short period. However a flash period with a duration of 1 ms is too short to enable the occurence of longer chains of photochemical reactions inthe gas phase or between gas and the surface of particles.

The lamp 4 is arranged in an intermediate chamber 14 which is defined by a portion 5 of the wall of the chamber 3 as well as by two light barrier means 6a and 6b. The chamber 14 is illuminated by the lamp 4 situated therein. The illuminated part of the wall portion 5 of the chamber 3 as well as those portions of the light barries 6a and 6b which are subjected to the radiation of the lamp 4 are of such a configuration that no photoemission can occur under the influence of the radiation. It is understood that a development and evolution of additional photo electrons would result in the fact that these electrons and the negative ions formed therefrom in the gas, respectively, accumulate on the particles and thereby compensate or overcompensate the positive charge due to the photoemission.

The electrons emitted from the particles move to the wall portion 5 because of their high diffusion coefficient. It is thereby required that the wall portion 5 in the illuminated chamber 14 has, at least partially, a conductivity which allows removal of charges diffusing thereto. The wall portion 5 being without this quality, it would have to be expected that uncontrolled electrical fields occur in the illuminated zone of the chamber 14 under the influence of the accumulating negative charge which leads, in turn, to uncontrolled and unpredictable precipitation of charged particles. The photo emission from the wall portion 5 may be avoided by providing a layer of insulating material on the surface of the wall portion 5, e.g. consisting of lacquer or grease. If such insulating material is applied sufficiently thin to the conductive wall surface (e.g. with a thickness of 1 micron), charge transport through this layer to the wall surface is sufficiently ensured.

The aerosol to be characterized enters the chamber 3 through the inlet portion 1 and is initially fed to a neutralization zone 7 prior to be photoelectrically charged. In the neutralization zone 7 a well defined initial distribution the charge of the particles is established. One possibility to operate the neutralization zone 7 consists in enriching the aerosol with an identical number of positive and negative small ions. According to the theory probability, these small ions accumulate on the particles and thereby a well defined charge distribution is established. If air used as a carried gas, this may simply be done by means of a radioactive radiation source 15 which ionizes the air sufficiently. Another possibility is to remove all charged particles from the aerosol by an electrical field.

The neutralization zone 7 and the illuminated zone 14 further include heating means, e.g. in the form of a heater filament 8 shown in FIG. 1. The main purpose of the heating means is to modify the particle surface in a controlled way, i.e. to remove components quenching photoemission (typically at about 100° C) and/or to remove or decompose components exhibiting or promoting photoelectric activity. The heating means are developed such that variation of the temperature of the particle carrying gas is possible in order to allow determination of the output signal dependence on temperature. By evaluating such dependence in comparison with the known scale of evaporation temperatures constituted by the substances possibly present on the aerosol particles or being of special interest and with taking in consideration known photoelectric characteristics of such substances, the actual presence thereof as well as the relative amounts or particle numbers can be determined.

In view of the desired unambiguous coordination between evaporation temperatures of specific substances and the corresponding charge measuring values, for adjusting as well as varying the aerosol temperature, generally stationary conditions have to be established. Therefore, a mode of operation is preferred in which said aerosol is heated in consecutive processing stages to a plurality of temperature levels. Each such processing stage comprises activating aerosol particles to electron emission and measuring the electric charge of the particles. Stationary conditions can be readily achieved in each such processing stage. However, different modes of operation are applicable also, depending on the specific conditions and aims. In many cases the method may be carried out by heating the aerosol so as to create an at least temporarily continuous temperature increase, the rising rate of which is held below a limit value sufficiently low for establishing approximately stationary values in the charge measuring.

In order to render possible a well-defined determination and variation of the aerosol temperature, the apparatus of FIG. 1 comprises a feed-back control loop including temperature sensing means 101, e.g. a thermocouple, located in the range of the outlet of said illuminated zone 14 and connected to the input of a power amplifier 102 delivering a signal voltage $U_t$ representing the actual temperature value and loadable enough to feed a temperature display 103 as well as the inverting input, i.e. the actual value input, of a controlled 104. For delivering the temperature command value to the noninverting input of controller 104 an adjustable voltage divider 105 fed by a highly stabilized DC source 106 is provided. The output of controller 104 actuates a power switch 107 connecting an AC source 108 to said heater filament 8.

A secondary purpose of the heating means is to reduce the relative humidity of the aerosol. Thereby condensation of water in the chamber 3 is avoided. In particular, condensation on insulations 12a and 12b would falsify the finally required output signal of the apparatus. Particularly it has to be noted that the finally measured values are independent of the humidity of the atmosphere by these measures, if the apparatus of the invention is used outside a building. If the lamp 4 develops enough heat, this energy may be used to heat the carrier gas, thereby removing the need to provide separate heating means 8. However, a condition is that the heat conductivity through the walls of the chamber 3 and thereby the convection to the ambient is low as compared to the heat developed by the lamp 4. For instance, a wall of the chamber 3 made of stainless steel has a comparatively low heat conductivity.

In the region of the outlet portion 2 of the chamber 3 a fan 9 with a speed-controllable DC motor 9a is provided. It forces the carrier gas containing the aerosol to flow from the inlet portion 1 to the outlet duct in the region of the outlet opening 2. Adjustment of the aerosol flow is facilitated by a variable resistor 109 connecting motor 9a to its current source 110.

Downsteam of the chamber 14 providing the photoelectric charge of the particles, a first collector electrode 10a is mounted which is used to colled part of the charged particles. The latter ones transfer their charge to the collector electrode 10a. Under stationary operational conditions, i.e. with a constant potential value of electrode 10a, the discharge current thus established is representative of the number of particles collected per time on electrode 10a. The discharge current is measured in a sensitive current meter 11a connected to said electrode. The latter one may consist of a size-selective filter element including a cluster or a web of filaments mounted in a perforated metal casing. The metal casing of the electrode 10a is connected to the wall of the chamber 3 by means of an insulating ring menber 12a in such a way that the flow of the carrier gas is forced to pass the filter element of electrode 10a.

The probability that a particle is deposited in the filter depends on its diffusion constant which, in turn, depends on the size of the particle. Smaller particles have a higher diffusion velocity, resulting in a higher probability that they are deposited in the filter. The probability that a particle is deposited in the filter is increased, if the filaments of the cluster or web of the filter are arranged tightly to each other. Besides diffusion, inertia of the mass of the particles may play an important role. The characteristics of the filter with respect to size-dependent penetration and deposition of the particles is determined by its geometry. In a preferred embodiment the filter may be designed such that the penetration characteristics correspond to the ones of the human lung. Consequently the signal measured by the current meter 11a corresponds to the amount of the hydrocarbon containing particles deposited in the human lung.

If a sequence of several filters is used, wherein each following filter is finer than the preceding one, it is possible to simulate deposition of particles along the human breathing path. The embodiment shown in FIG. 1 incorporates a second colector electrode 10b serving as a second filament filter, which is so finely woven that all remaining particles are deposited therein. The current thereby created its measured by a second meter 11b connected to the second collector electrode 10b.

It is also possible to provide a further size-selective filter in front of the first filter serving as collector electrode. Such further size-selective filter will not be used as a further collector electrode and, consequently, it is neither electrically insulated from the housing of the chamber 3 nor connected to a current meter.

The filament filters may consist of metallic filaments or wires which are woven into the shape of grid-like elements. However it is not necessary to use electrically conductive filament material. The same effect may be attained if filter elements made of cellulose or plastic material are used, like the ones currently used in breathing filters, if they are mounted in a metallic casing, serving as a Faraday cage. Diffusion batteries may be used as size-selective filters instead of filament filters as well. A diffusion battery consists, for instance, of a number of parallely arranged plate member having a distance between each other in the range of 1 mm, the aerosol flowing between said plate members.

The insulating ring menbers 12a and 12b mounting the collector electrodes 10a and 10b to the wall of the chamber 3 must have a water-repulsive surface. This means that the surface are hydrophibic and are not wet by water. Such a behaviour would result in surface conductivity depending on the relative humidity of the aerosol. Ir was possible to show that reliable, moisture-independent measurements can be made by using insulating member 12a and 12a made of Teflon (Registered Trade Mark) or made of glass or ceramic elements which are covered by a layer of Teflon (Registered Trade Mark).

In front of and behind the collector electrodes 10a and 10b, there electrostatic shielding screen members 13a and 13b are provided, serving as shields for the electrodes 10a and 10b against interferences produced by the lamp 4 or the fan 9.

As far as the interpretation of the measured values is concerned, the following remarks have to be duly considered: The currents or charges which have been measured depend, among others, on the efficiency of photoelectric charging. The latter one is a function of the time during which the particles are subjected to radiation in the illuminated zone 14; with other words, the measured signal depends on the flow velocity. At short radiation times, the number of electrons photoemitted by particles is proportional to the emission rate and to the radiation period (linear region). A particle already having emitted some electrons will not emit further electrons as easily as the previously emitted ones, since its positive charge hingers further electron emission by action of the Coulomb force. Consequently, the particles, having been subjected to a radiation during an extended period, reach a condition of maximum charge (saturation). By means of varying the flow velocity the desired region (linear region, intermediate region or saturation) may be selected. Within the linear region the signal at the collector electrodes is proportional to and gives a value corresponding to the photoelectric activity of the aerosol, while the signal in the region of saturation indicates the total number of PAH-coated particles, however in relation to a size-dependent factor (maximum possible charge).

Figure 2:
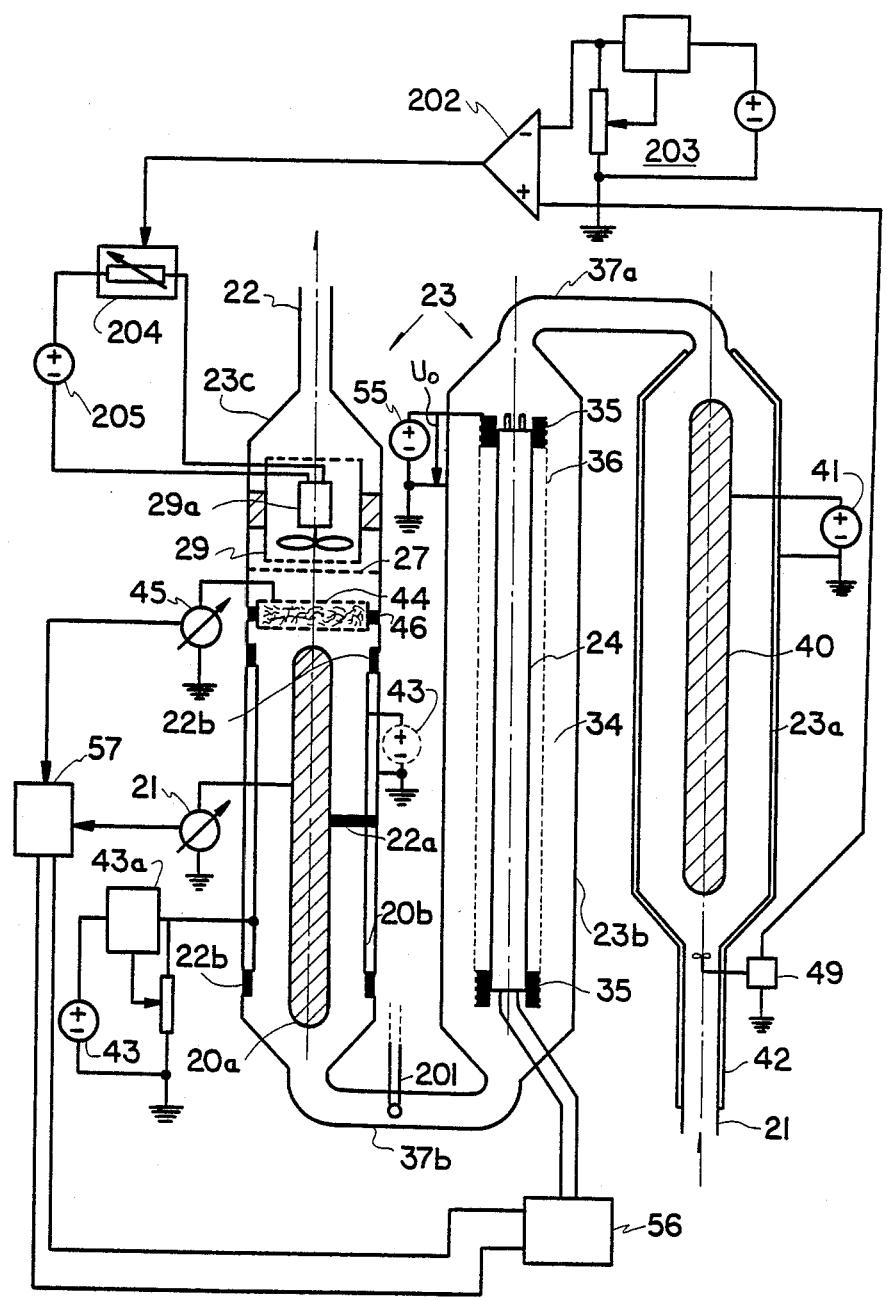
FIG. 2 shows a representation similar to the one according to FIG. 1 of a second embodiment.

The embodiment of the apparatus according to the invention shown in FIG. 2. comprises a generally tubular chamber 23, through which the aerosol to be investigated flows from an inlet 21 to an outlet 22 due to the action of a fan 29 arranged upstream of said outlet and driven by a DC motor 29a. In a sequence according to the flow of the aerosol, chamber 23 is subdivided into three zones, i.e. a first or neutralization zone 23a, a second or illumination zone 23b and a third or measuring zone 23c. These zones are formed as tube sections of cylindrical shape. The walls of chamber 23 are electrically conductive and connected to ground.

A flow meter 49 of a kind well-known in the art is arranged downstream of the air inlet 21. For the purposes of the invention in certain cases it is essential that a desired flow velocity can be selected and maintained by appropriate speed control of the fan 29. Therefore, in the example shown in FIG. 2 the output flow meter 49, which delivers a voltage signal representative of the actual mass flow of the entering aerosol, is connected to the actual value input of a controller 202, while the command value input thereof is connected to adjustable DC voltage source means 203. The output of controller 202 actuates a variable resistor 204 inserted in the DC feed circuit of fan motor 29a. All these control means are well-known per se in the art and need no further explanation.

The first zone 23a is substantially formed as a capacitor with a cylindrically shaped inner electrode 40 and with the wall of said zone 23a as the outer electrode. A high voltage source 41 connected between both electrodes can be adjusted in such a way that essentially all charged particles are removed from the entering aerosol. Thus zone 23a serves as a neutralization means.

As explained already with regard to the example of FIG. 1, heating the aerosol to a well-defined temperature level or in accordance with a predetermined variation so as to modify the surface of the aerosol particles is essential for the detection of PAH. Therefore, appropriate heating means acting on the aerosol before photoelectric activation are provided here also. In the example, this is an electric heating filament 42 surrounding the inlet 21 and the first portion 23'a of chamber 23. Furthermore, temperature sensing means 201 are provided in the section of chamber 23 between zones 23b and 23c. The aerosol temperature thus detected comes very close to the relevant value, i.e. the one prevailing during the photoelectric activation of the particles. Appropriate adjustment and control means for maintaining the desired aerosol temperature are provided here also as in the example of FIG. 1, but no more shown in detail again.

The second zone 23b comprises a longitudinal, tubular lamp 24 mounted therein coaxially to its longitudinal axis, thus forming an illuminated space 34. An ozone-free mercury low-pressure lamp emitting a radiation with a wavelength of 254 nm may be used. The lamp 24 is surrounded by an electrical screen member 36 mounted on the lamp by means of annular insulating members 35. The screen member 36, which may have a wired structure, prevents erratic electric fields caused by charging of the glass envelope of the lamp 24 from penetrating the region of flow of the aerosol. An electric field extending radially between the screen member 36 and the grounded wall of zone 23b may be established in the illuminated space 34 by feeding the screen member 36 with an electric voltage $U_o$ supplied by a DC source 55. If this voltage is comparatively low (e.g. in the region of 10 V), and if the typical flow velocity is about some cm per second, all photoelectrons and the negative ions formed therefrom, respectively, are removed from the aerosol, without removing the charged particles which are much more immobile. Thereby a reduction of the lifetime of negative charge carriers and, simultaneously, an increased efficiency of charging is realized, since the probability of reattachment on the particle is minimized.

The same effect may be attained if $U_o$ is an AC voltage, assuming that the ratio between voltage and frequency is chosen such that the ions are deposited within half a period at the screen or at the chamber wall, while the charged particles perform only a slight oscillating movement.

The surface of the chamber wall in the illuminated space 34 as well as the screen 36 are coated with a thin layer of insulating lacquer in order to prevent any photoemission.

On both ends of the second zone 23b the walls of chamber 23 have a decreased diameter and merge into two curved tube portions 37a and 37b, the inner wall surface thereof being coated with a non-reflective material. These tube portions serve as light barriers or sluices and prevent photoemission from the following components. Furthermore, the electrically conductive wall of the narrowed tube section 37b offers a sufficient electrostatic shielding with reference to the installations following downstream.

The third zone 23c comprises an elongated, cylindrical collector electrode 20a arranged centrally and coaxially therein and which is connected to the wall of said zone 23c by means of a Teflon-coated ceramic rod 22a. A cylindrically shaped electrode 20b surrounding the collector eletrode 20a is provided within the zone 23c and connected to the wall thereof by means of two insulating annular members 22b. The electrode 20b and the collector electrode 20a together form a measuring capacitor. The collector electrode 20a is connected to ground via a current meter 21 and, therefore, has ground potential. The electrode 20b is connected to ground via a highly stabilized DC voltage source 43 (e.g. a battery having a voltage of 100 V) establishing a positive potential thereon. Thus, the aerosol particles bearing a positive charge due to the photoelectrically induced electron emission are drawn to the collector electrode 20a and deliver their charge thereto. A closed current measuring circuit through voltage source 43, current meter 21 and said measuring capacitor is established. The current which flows therethrough under the stationary conditions due to the constant voltage over the measuring capacitor maintained by source 43 offers a measuring value representative of the charge deposited per time on the collector electrode 20a and of the number of charged aerosol particles per time delivered by the illuminated zone 23b and discharged in the measuring capacitor.

The voltage applied to the measuring capacitor with electrodes 20a and 20b can be adjusted in such a way that only the smaller particles, i.e. those particles having a higher electrical mobility, are deposited and discharged on the collector electrode 20a. This means that the measuring capacitor serves as a size-selective electric filter. By periodically changing the value of voltage source 43 different sizes can be selected. For this purpose source 43 is provided with appropriate control means, e.g. with an adjustable voltage regulator 43a of a kind known per se as indicated in FIG. 2.

A second collector electrode 44 formed as a filament filter and connected to a current meter 45 is arranged downstream of the measuring capacitor and mounted to the wall of zone 23c by means of a Teflon-coated annular member 46 made of glass. Said filament filter is of a very fine configuration so that all remaining particles are collected by this filter. Consequently, the current indicated by the meter 21 corresponds to the flow of the smaller particles and the current indicated by the meter 45 corresponds to the flow of the larger particles contained in the aerosol.

In order to avoid disturbances, the second collector electrode 44 is shielded from the fan 29 by a screen grid 27.

Particularly the apparatus shown in FIG. 2 may be constructed according to a a very compact design, e.g. as a portable apparatus, and is particularly suitable to measure air pollution caused by carbonacious hydrocarbon containing particles. Two different size classes are indicated separately. For instance, the control means of voltage source 43 may be adjusted so that the current meter 21 shows the number of PAH-coated particles with a diameter of 10 to 100 nanometer, while the current meter 45 indicates the number of particles having a diameter of 100 to 1000 nanometer.

Current meters and charge meters with the required sensitivity show a more or less pronounced drift of the zero value during extended measurement periods. If the value of the current or charge to be measured is small with reference to these drift fluctuations, it is imperative to re-calibrate the measuring equipment during the measuring procedure. This can be done by switching-off the lamp using lamp control unit 56 of FIG. 2, or by providing an electro filter in front of the collector electrodes, which is energized from time to time to remove all charged particles. The real value of the measurement can be calculated from the difference between the two indications of the meter.

In addition, it must be considered that fluctuations of the measured values which are not related to a mean value and which are caused by interferences, noise of electronic components or fluctuations of the concentration of aerosol particles, can not be avoided. However such fluctuations may be reduced by calculating the mean value with reference to the measurement period. In the so-called "lock-in-technique" this is done by inversion of the polarity in phase with the switching-on and switching-off and by determination of the mean value. In other words, the signal is correlated with the clock period of the switching sequence, and the mean time value is produced. It is understood that the correlation must be effected with a suitable phase difference since a certain time passes between the flowing of the aerosol through the switched element (lamp chamber or electric filter) and the collector electrode. This is achieved by computing means 57 connected to the current meters 45 and 21 and to the lamp control unit 56. By controlling the heater 42 also by this computing means, the signals can be measured also as a function of temperature. This yields further information on condensates on the particle surfaces.

Figure 3:
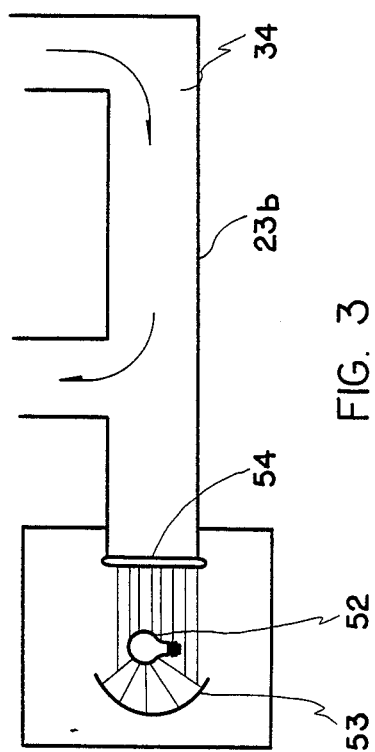
FIG. 3 shows a partial sectional view of a modified processing chamber including the irradiation zone.

In FIG. 3 there is shown a further embodiment which could be used as a modification of that part of the chamber 23b of FIG. 2 which includes the illuminated zone 34. A lamp 52 and a spherical mirror 53 are protected from the gas flow indicated by arrows by means of a quartz window 54. The mirror 53 creates an essentially parallel light bundle within the zone through which the gas flows.

Figure 4:
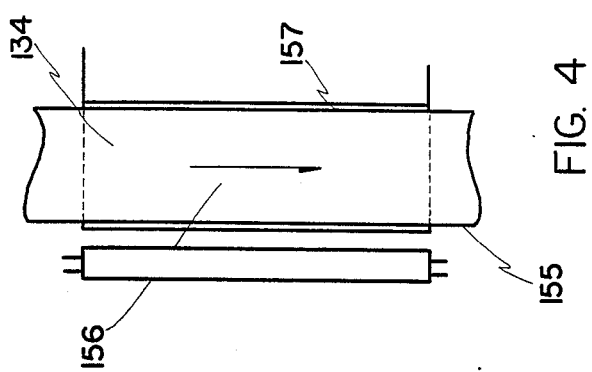
FIG. 4 shows a further modification of the irradiation zone.

In FIG. 4 another modification of the part of chamber 23b according to FIG. 2 is shown which there includes the illuminated zone 34, which allows a very simple setup. The illuminated zone 134 of FIG. 4 is formed by a tube 155 made of a material which allows the light from an externally mounted lamp 156 to enter into tube 155. The separation of lamp and illuminated zone is of great advantage because tube 155 can now be heated by an appropriate heater 157 to high temperatures without destroying the lamp.

What we claim is:

1. A method for the characterization of particles in aerosol, comprising:
    using an aerosol, which has been brought to at least one predetermined temperature sufficient for evaporation or decomposition or preventing condensation of molecules on particles of said aerosol;
    exposing said aerosol to an electromagnetic radiation for activating particles contained in the aerosol to cause said aerosol particles to emit electrons and attain an electric charge correspondingly; and
    measuring the electric charge of said aerosol particles.

2. A method for the quantitative and qualitative characterization of hydrocarbon containing particles in an aerosol, comprising:
    using an aerosol, which has been brought to at least one predetermined temperature sufficient for evaporation or decomposition or preventing condensation of molecules on particles of said aerosol;
    exposing said aerosol to an electromagnetic radiation having photon energies which are below the ionization energy of the carrier gas of the aerosol and above the work function of said aerosol particles for activating said aerosol particles to cause said aerosol particles to emit electrons and attain an electric charge corresponsingly; and
    measuring said electric charge of said aerosol particles.

3. Method according to claim 1, wherein ultraviolet radiation is used for activating aerosol particles.

4. Method according to claim 1, in which said aerosol is exposed to said radiation, while being at a temperature sufficient for evaporation or decomposition or preventing condensation of molecules on particles of said aerosol.

5. Method according to claim 1, in which a flow of said aerosol with a predetermined flow rate is established and subjected to heating and said activating radiation, and said charge measuring being carried out under stationary temperature conditions in the aerosol.

6. Method according to claim 1, in which said aerosol is heated in consecutive processing stages to a plurality of temperature levels, wherein each such processing stage comprises activating aerosol particles to electron emission and measuring the electric charge of the particles thus achieved.

7. Method according to claim 1, in which said aerosol is heated so as to create an at least temporarily continuous temperature increase, the rising rate of which is held below a limit value sufficiently low for establishing approximately stationary values in said charge measuring.

8. Method according to claim 1, in which said molecules to be evaporated, decomposed or prevented from condensation are capable of quenching the photoelectric activity of said particles.

9. Method according to claim 8, in which said molecules are non-aromatic hydrocarbons or derivates thereof.

10. Method according to claim 8, in which said molecules are inorganic acids.

11. Method according to claim 8, in which said molecules are water.

12. Method according to claim 1, in which said molecules to be evaporated, decomposed or prevented from condensation are capable of enhancing the photoelectric activity of said particles.

13. Method according to claim 12, in which said molecules are aromatic hydrocarbons or derivates thereof.

14. An apparatus for characterization of particles in an aerosol, said apparatus comprising:

an essentially closed chamber comprising a gas inlet, a gas outlet, and means for establishing an aerosol flow through said chamber;

means mounted in the interior of said essentially closed chamber in the region of said inlet for electrically neutralizing said aerosol;

means for heating said aerosol, said heating means comprising measuring and control means for establishing a predetermined aerosol temperature;

radiation means arranged within the interior of said essentially closed chamber and defining an irradiation zone for activating the heated aerosol flowing therethrough;

said irradiation zone comprising a wall surface held at a defined electric potential and having a conductivity which is high enough to conduct the charge of ions produced by irradiation and movable to said wall surface to said defined electric potential; and at least one collector electrode mounted in the interior of said essentially closed chamber downstream of said irradiation zone for collecting electrically charged particles and electrically connected to a current or charge meter;

said at least one collector electrode comprising a size selective particle filter mounted downstream of said irradiation zone and arranged in the flow of said aerosol, said size selective particle filter comprising an electric capacitor having two electrodes in spaced relationship and an electric field between said two electrodes, said aerosol flowing through the space between said two electrodes and said electric field having a magnitude which is high enough to deposit at least a part of the charged particles of said aerosol on the negative electrode of said capacitor, and control means connected to said electrodes of said capacitor in order to periodically change the field strength of said electric field between a lower value and a higher value.

15. An apparatus for characterization of particles in an aerosol, said apparatus comprising:

an essentially closed chamber comprising a gas inlet, a gas outlet, and means for establishing an aerosol flow through said chamber;

means mounted in the interior of said essentially closed chamber in the region of said inlet for electrically neutralizing said aerosol;

means for bringing said aerosol to at least one predetermined temperature sufficient for evaporation or decomposition or preventing condensation of molecules on particles of said aerosol;

radiation means arranged within the interior of said essentially closed chamber and defining an irradiation zone for activating the heated aerosol flowing therethrough;

said irradiation zone comprising a wall surface held at a defined electric potential and having a conductivity which is high enough to conduct the charge of ions produced by irradiation and movable to said wall surface to said defined electric potential; and at least one collector electrode mounted in the interior of said essentially closed chamber downstream of said irradiation zone for collecting electrically charged particles and electrically connected to a current or charge meter.

* * * * *